US006852681B1

(12) United States Patent
Kerschner et al.

(10) Patent No.: US 6,852,681 B1
(45) Date of Patent: Feb. 8, 2005

(54) COMPOSITIONS AND PROCESS FOR PREPARING CLEANSING BARS COMPRISING LOW LEVELS OF SOLUBLE SURFACTANT FOR ENHANCED FRAGRANCE DEPOSITION/LONGEVITY

(75) Inventors: Judith Lynne Kerschner, Hawthorne, NJ (US); Georgia Shafer, West Caldwell, NJ (US); Charles Craig Nunn, Rutherford, NJ (US); Terence James Farrell, Tenafly, NJ (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/756,617

(22) Filed: Jan. 13, 2004

(51) Int. Cl.[7] .................................................. A61K 7/50

(52) U.S. Cl. ....................... 510/152; 510/151; 510/153; 510/155

(58) Field of Search ................................ 510/141, 151, 510/152, 153, 155

(56) References Cited

U.S. PATENT DOCUMENTS 5,262,079 A * 11/1993 Kacher et al. .............. 510/146
5,387,362 A 2/1995 Tollens et al.
5,540,852 A * 7/1996 Kefauver et al. ........... 510/152
6,143,704 A * 11/2000 Van Gunst et al. ......... 510/152
6,242,399 B1 * 6/2001 Chambers et al. .......... 510/154

OTHER PUBLICATIONS

U.S. Appln. No. 10/756,616, filed Jan. 13, 2004, Farrell et al.
U.S. Appln. No. 10/756,615, filed Jan. 13, 2004, Farrell et al.

* cited by examiner

*Primary Examiner*—Necholus Ogden
(74) *Attorney, Agent, or Firm*—Ronald A. Koatz

(57) ABSTRACT

The invention relates to perfume-containing bar compositions in which the effect of said perfume(s) (e.g., longevity) is enhanced relative to comparative bars in that perfume-containing bar of the invention, comprise less than about 35% soluble surfactant. The invention further comprises a process for enhancing deposition/longevity of perfume, for example, by controlling the level of soluble active relative to insoluble active and/or by increasing levels of perfume.

9 Claims, 8 Drawing Sheets

Figure 1: Perfume extraction data of the solution and solid phases of a 5% solution of 85/15 soap.
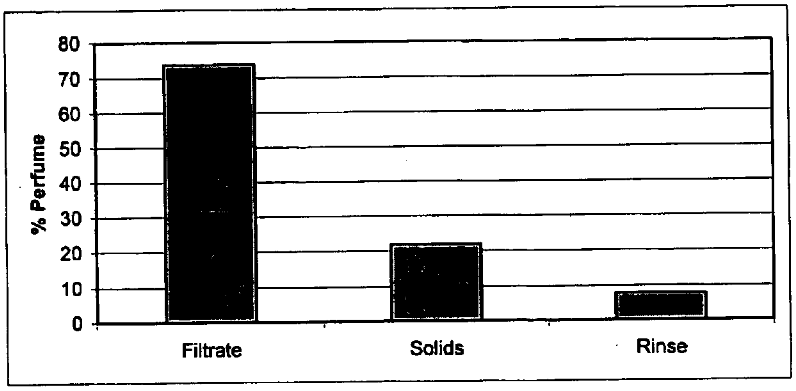

Figure 2: Effect of surfactant:perfume ratio on performance of individual perfumes
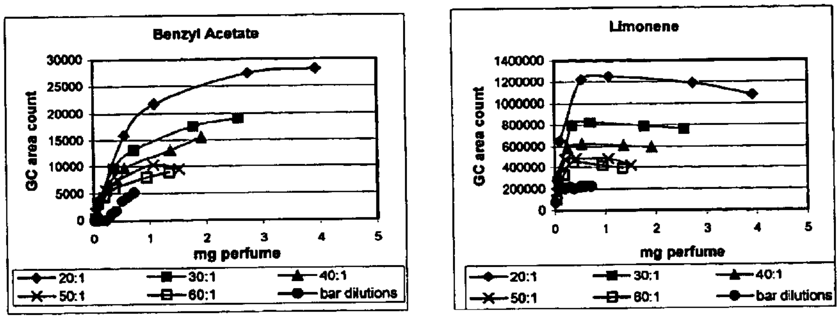

Figure 3: Effect of surfactant:perfume ratio on perfume performance in 2:1 model system
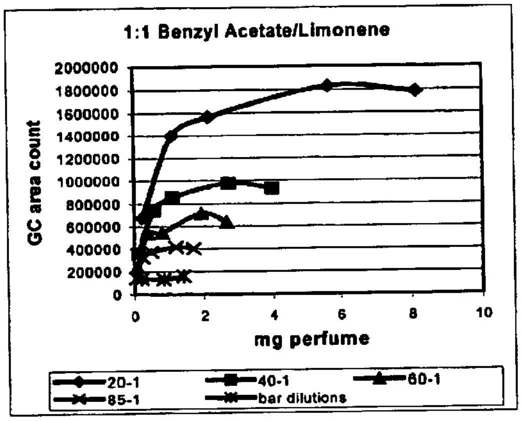

Figure 4: Predicted values (solid lines) vs. experimental results (symbols) for benzyl acetate in surfactant solutions with increasing surfactant to perfume ratios
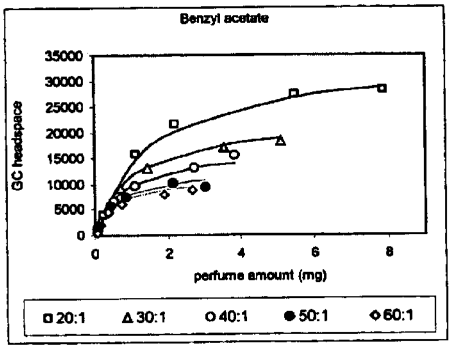
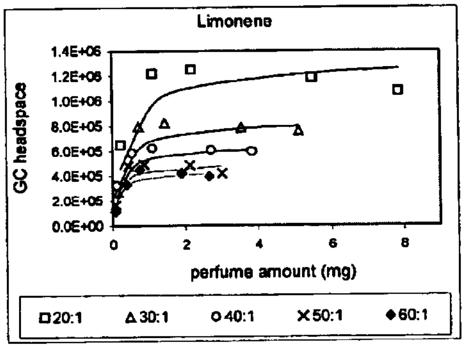

Figure 5: GC headspace data for soap systems with different solids levels.
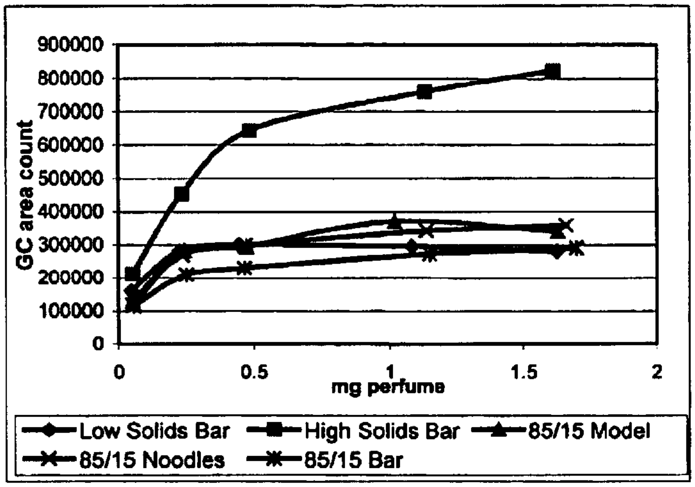

Figure 6: GC data comparing a soap bar with 1% perfume to a soap bar containing 4% perfume.
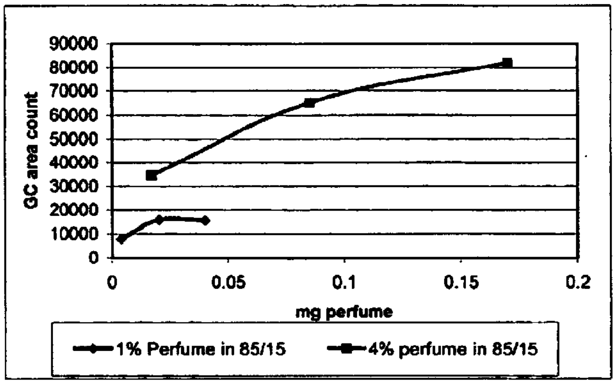

Figure 7: SPME data for arms washed with the "high solids" bar vs. an 85/15 bar
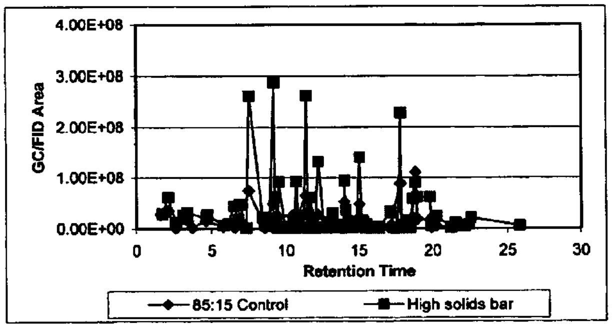

Figure 8: SPME data comparing arms washed with a soap bar with 1% perfume and with 4.5% perfume
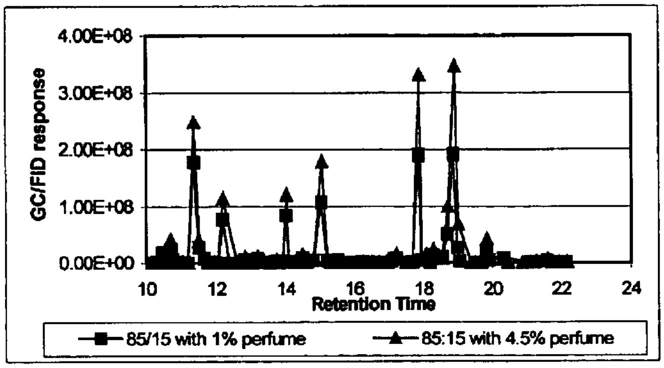

COMPOSITIONS AND PROCESS FOR PREPARING CLEANSING BARS COMPRISING LOW LEVELS OF SOLUBLE SURFACTANT FOR ENHANCED FRAGRANCE DEPOSITION/LONGEVITY

FIELD OF THE INVENTION

The present invention relates to delivery of perfume performance from cleansing bar systems. Specifically, it relates to a process for enhancing perfume performance (measured as perfume enhancement factor or "PEF") by formulating bars in such manner as to decrease the soluble surfactant to perfume component(s) ratio. The ratio of soluble surfactant to perfume component in the bar can in turn be controlled by decreasing level of soluble surfactant (e.g., by controlling amounts of generally less soluble, saturated, longer chain length fatty acid or fatty acid soaps versus amounts of generally more soluble, saturated, shorter chain length fatty acid or fatty acid soaps); and/or by increasing level of perfume.

BACKGROUND

Soap bars consist of a blend of different chain length fatty acid soaps. Some of the fatty acid soaps (e.g., typically shorter chain length $C_{14}$, $C_{12}$ and below as well as some unsaturated soaps, such as oleate) from which the bars are made are soluble (by "soluble" is generally meant it dissolves at greater than 1 wt. % level in water at less than about 40° C.; it should be understood that solubility may refer to single soaps/surfactants or to mixtures/complexes of soaps and/or surfactants which, as a mixture or complex, have solubility within the defined parameters); and some (e.g., $C_{16}$, $C_{18}$ and higher chain lengths) are insoluble or substantially insoluble (again insolubility may refer to mixtures or complexes).

A "typical" soap bar consists of mixtures of saponified nut oils (generally producing more lower chain length, soluble fatty acid soaps) and saponified non-nut oils (generally producing more higher chain length, insoluble fatty acid soaps) which will comprise the various chain length fatty acid and various saturated and unsaturated fatty acid soaps. A typical 85/15 bar, for example, is 85% tallow (comprising longer chain soaps generally required for the structuring when bars are extruded) and 15% coconut (containing shorter, more soluble soaps which yield good foam and other attributes). Such 85115 soaps will generally contain about 50–60% soluble actives.

Applicants have now found that, when the level of soluble actives is kept low (e.g., below about 35% by wt. of bar composition, more preferably below 30% by wt., even more preferably below about 25% of final bar being soluble active, active being soap or synthetic surfactant), then the fragrance delivery is enhanced relative to delivery of fragrance from a bar having higher levels of soluble active in the final bar. In one embodiment of the invention, the bar with low levels of soluble active is predominantly a soap bar or bar comprising a mixture of soap and free fatty acid but, as noted, the bar can be any bar where the amount of the soluble surfactant (e.g., soap, synthetic) is kept at a level of below about 35% by wt. of final bar.

There are a number of references which disclose compositions having mixtures of short and long chain, saturated and unsaturated fatty acids possibly mixed with variety of ions to form soaps. No art of which applicants are aware, however, discloses the criticality of maintaining levels of soluble active below certain level (35% of total active) to enhance perfume delivery or a process/method of enhancing such delivery using the specific compositions of the invention.

U.S. Pat. No. 5,387,362 to Tollens et al. discloses compositions containing a tailored mixture of Mg, Na and K ions reacting with lauric acid, select $C_{14}$–$C_{18}$ fatty acids as well as oleic acid to generate soap base. A related reference is U.S. Pat. No. 5,540,852 to KeFauver et. al. There is no disclosure in either reference of compositions with perfume and levels of soluble soaps which must be below certain levels; nor a disclosure of a process for enhancing perfume delivery (e.g., enhanced PEF). Indeed, there is no recognition of preparing bars to ensure the level of soluble soap must comprise no higher than 35% of total surfactant.

U.S. Pat. No. 5,262,079 to Kacher et al. discloses partially neutralizing fatty acids to form a network for a framed bar and also contains high levels of anionic surfactant plus nonionic firmness aids. There is no discussion of compositions with perfume and levels of soluble active below certain level or of processes to enhance perfume delivery. That is, there is no direction or suggestion to prepare bars to ensure final level of soluble active is no more than 35% of total actives. The reference also relates to framed bars versus extrusion bars of the subject invention.

U.S. Pat. No. 6,121,216 to Narath et al. discloses a way to improve processing of a syndet bar which incorporates amphoterics as a mildness aid. Processing efficiency is increased by minimizing levels of soap, especially unsaturated soaps. That soluble active must comprise less than 35% of total active and the influence of such low level on perfume enhancement are not disclosed.

BRIEF DESCRIPTION OF THE INVENTION

In one embodiment the subject invention relates to compositions for enhancing deposition of perfume molecule(s) which comprises:

A bar composition comprising:

(1) detergent active where no more than about 35% by wt., preferably no more than about 30% by wt. of total bar composition comprises soluble surfactant active (e.g., bar may comprise 0.5–35%, preferably 1.0 to 30% by wt. soluble active); and (2) perfume active or actives, wherein said composition provides enhanced delivery of perfume relative to bar composition having greater than about 35% soluble surfactant actives;

wherein solubility is defined by dissolution of surfactant actives or active combination (e.g. if combination has higher solubility than individual components) of greater than about 1% by wt. in water at 40° C.

The remainder of bar (e.g., 0.1 to 65% by wt.) may comprise 0.5 to 20%, preferably 0.5 to 15% by wt. water and 0.5 to 99%, preferably 1 to 70% by wt. of "filler materials".

Such filler materials may range from anything which can hold together or "structure a bar" including insoluble actives (insoluble soaps and/or fatty acids), organic and inorganic structurant materials and any one of thousands or more of materials which can be used as bar components.

The only criticality is that soluble surfactant comprise no more than 35% of bar by wt. and that the bar is solid enough to function as a "bar" (e.g., have yield stress of at least 90 kPa as measured by standard cheese-wire method with a 200 g weight and cheese wire diameter of 0.5 millimetres).

In a second embodiment, the invention comprises a process for enhancing perfume retention/longevity of perfume which process comprises minimizing the level of soluble surfactant actives in a bar relative to a typical bar comprising greater than about 35%, generally comprising 40–70%, soluble surfactant active.

In a particular embodiment of the invention the invention relates to bar compositions comprising:

(1) 20% to 75% fatty acid soap and free fatty acid mixture (most of which is insoluble but some of which may be soluble);

(2) 0% to 20% synthetic surfactant active; and (3) balance water, minors and fillers/other bar components, wherein the percent of active (1) and (2) which is soluble is less than about 35% by wt. total bar composition; and wherein PEF ≧ to about 2.2, preferably greater than 2.3, more preferably greater than 2.5 relative to a standard control (for example 85115 soap bar).

BRIEF DESCRIPTION OF THE FIGURES

FIG. 1 is a graph showing the fraction of soap into which the perfume partitions. The graph shows that most perfume by far will partition into the soluble filtrate. While not wishing to be bound by theory, it is for this reason that it is believed percent of soluble surfactant should be minimized, i.e., to minimize loss of perfume through soluble component, thereby making it unavailable for good perfume performance.

FIG. 2 is a graph of surfactant to perfume ratio and its impact on two different perfume components. Both components partition into the surfactant phase and therefore provide higher surfactant to perfume ratios (i.e., greater surfactant content), and perfume impact is reduced.

FIG. 3 is a graph of the effect of surfactant to perfume ratio on perfume performance for a 2:1 sodium oleate:sodium laurate system. Increasing surfactant:perfume ratio results in decreased perfume impact.

FIG. 4 is a graph of predicted impact measurements for benzyl acetate and limonene in surfactant solutions with increasing surfactant to perfume ratios. The higher the ratios, the lower the perfume impact.

FIG. 5 is a graph comparing GC headspace data of soap systems having dfferent solid levels. Generally, those with "high solids" (i.e. less amount of soluble soap) have significantly higher fragrance headspace. As such, again, bars with a lower amount of soluble soap will have greater perfume impact.

FIG. 6 shows GC data of two bar solutions at different dilutions, one with 1% perfume compared to one with 4% perfume. Raising level of perfume relative to surfactant also enhances perfume impact above the solution.

FIG. 7 shows the GC data from a SPME measurement of perfume deposited on the skin. This graph compares the deposition of perfume from a bar formulated with "high solids" (low soluble surfactant) and a control bar with low solids (high soluble active). Clearly the graph indicates more fragrance deposited to the skin from the "high solids" bar.

FIG. 8 shows the GC data from a SPME measurement of perfume deposited on the skin. This graph compares the deposition from a bar containing 1% perfume and a bar containing 4% perfume (same high soluble active formulation). Again the graph indicates that increasing the perfume:soluble surfactant ratio provides greater perfume deposition.

DETAILED DESCRIPTION OF THE INVENTION

The present invention relates to bar compositions comprising perfume and to processes for enhancing perfume retention/longevity using bar composition having no more than a defined amount of soluble active as a percent by wt. of total bar. The soluble surfactant active is believed to enhance perfume partitioning into the active thereby reducing available perfume and decreasing perfume performance.

Another way of defining a low level of soluble active is to define a soluble surfactant:perfume ratio. Specifically, activity or impact of perfume can be seen to increase as the ratio of surfactant to perfume decreases. While such ratio from a "typical" soap bar may be 60:1, the compositions of the subject invention have ratios less than 40:1, preferably lower than 35:1, more preferably less than 30:1 and more preferably lower than 25:1. The lower the ratio, the greater the perfume impact.

The ratio in turn can be decreased either by decreasing the level of soluble surfactant (including synthetics and/or soluble soap), as has been noted, and/or by increasing the level of perfume.

The crux of the invention is therefore really that the total amount of soluble surfactant in the final bar composition be below about 35% of the bar composition because it is into the soluble surfactant (rather than any insoluble surfactant) that perfume will more readily partition in use, more readily wash off and ultimately reduce the perfume performance.

The type of soluble surfactant is therefore really irrelevant other than the fact that a soluble surfactant (or mixtures or complexes of surfactants) is/are defined as one(s) that have/has a solubility in water greater than 1 wt. % at temperature of 40° C. If the surfactant(s) does not meet this solubility limitation, there is therefore no limit on the amount of "insoluble" surfactant which can be used. It is for this reason that increasing the amount of insoluble surfactant relative to soluble surfactant (or conversely decreasing the amount of soluble surfactant in the bar composition) is one way of increasing the fragrance performance (e.g. fragrance deposition or fragrance longevity in use).

An example of how this works is if we consider a blend of dfferent chain length fatty acid soaps. As indicated above, shorter chain length fatty acid/fatty acid soap (e.g., typically shorter than $C_{16}$, particularly shorter than $C_{14}$) are "soluble" (and hence are also sometimes considered "harsher") while, for example, $C_{16}$ and above chain length saturated fatty acids/fatty acid soaps are typically insoluble. By increasing the ratio of longer chain length to shorter chain length saturated soaps (as applicants have done for different reasons in copending, co-filed application relating to fatty acid/fatty acid soap based bars with relatively low synthetic), it is possible to enhance perfume longevity or effect.

In particular, in one embodiment of the invention comprises:

(1) 0.5–35% by wt. soluble surfactant/actives;

(2) perfume;

(3) 0.5–20%, preferably 0.5 to 15% by wt. water; and (4) 0.1 to 99% by wt., preferably 1 to 70% by wt. fillers which may comprise structuring materials including insoluble actives and organic and inorganic materials which structure and fill.

The amount of soluble active/surfactant of (1) comprises no more than 35% by wt. of total bar, or the enhanced effect of the invention is not observed relative to bars having for example greater than about 35% soluble active. Stated differently, only those bars with soluble surfactant less than 35% by wt. of bar composition have performance enhancement factor of ≧2.2 PEF, preferably ≧2.3, more preferably ≧2.5 based on ratio of perfume deposited from bar relative to that deposited from a standard control.

Surfactant/Active

There is no constraint on what the active may be. It may be any of the myriads of anionic surfactants, nonionic surfactants, amphoteric/zwitterionic surfactants, cationic surfactants well known to those skilled in the art with the only criticality being that no more than 35% of active (including mixtures or complexes) may be soluble, wherein solubility is defined as at least 1% by wt. soluble in water at 40° C.

Perfumes

Perfume molecules include but are not limited to:

acetanisol; amyl acetate; anisic aldehyde; anisole; anisylalcohol; benzaldehyde; benzyl acetate; benzyl acetone; benzyl alcohol; benzyl formate; hexenol; d-carvone; cinnamaldehyde; cinnamic alcohol; cinnamyl acetate; cinnamyl formate; cis-3-hexenyl acetate; Cyclal C (2,4-dimethyl-3-cyclohexen-1-carbaldehyde); dihydroxyindole; dimethyl benzyl carbinol; ethyl acetate; ethyl acetoacetate; ethyl butanoate; ethyl butyrate; ethyl vanillin; tricyclo decenyl propionate; furfural; hexanal; hexenol; hydratropic alcohol; hydroxycitronellal; indole; isoamyl alcohol; isopulegyl acetate; isoquinoline; ligustral; linalool oxide; methyl acetophenone; methyl amyl ketone; methyl anthranilate; methyl benzoate; methyl benzyl acetate; methyl heptenone; methyl heptyl ketone; methyl phenyl carbinyl acetate; methyl salicylate; octalactone; para-cresol; para-methoxy acetophenone; paramethyl acetophenone; phenethylalcohol; phenoxy ethanol; phenyl acetaldehyde; phenyl ethyl acetate; phenyl ethyl alcohol; prenyl acetate; propyl butyrate; safrole; vanillin; viridine; allyl caproate, allyl heptoate, anisole, camphene, carvacrol, carvone, citral, citronellal, citronellol, citronellyl acetate, citronellyl nitrile, coumarin, cyclohexyl ethylacetate, p-cymene, decanal, dihydromyrcenol, dihydromyrcenyl acetate, dimethyl octanol, ethyllinalool, ethylhexyl ketone, eucalyptol, fenchyl acetate, geraniol, gemyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, napthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, verdox, allyl cyclohexane propionate, ambrettolide, Ambrox DL (dodecahydro-3a,6,6,9a-tetramethyl-naphtho[2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, citronellyl isobutyrate, citronellyl propionate, cuminic aldehyde, cyclohexylsalicylate, cyclamen aldehyde, dihydro isojamonate, diphenyl methane, diphenyl oxide, dodecanal, dodecalactone, ethylene brassylate, ethylmethyl phenylglycidate, ethyl undecylenate, exaltolide, Galoxilide™ (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, γ-ionone, α-irone, isobutyl benzoate, isobutyl quinoline, Iso E Super™ (7-acettl,1,2,3,4,5,6,7,8-octahydro,1,1,6,7-tetramethyl napthalene), cis-jasmone, lilial, linalyl benzoate, methoxy naphthaline, methyl cinnamate, methyl eugenol, γ-methylionone, methyl linolate, methyl linolenate, musk indanone, musk ketone, musk tibetine, myristicin, neryl acetate, δ-nonalactone, γ-nonalactone, patchouli alcohol, phantolide, phenylethyl benzoate, phenylethylphenylacetate, phenyl heptanol, phenyl hexanol, α-santalol, thibetolide, tonalid, δ-undecalactone, γ-undecalactone, vertenex, vetiveryl acetate, yara—yara, ylangene.

Filler

The "filler" material is everything else in the bar other than "soluble" surfactant, water and perfume or perfume ingredients. It should be understood that "filler" itself may be soluble and, as indicated above, is defined only as being something other than the specifically recited surfactant, perfume or water.

The structurant can be long chain, preferably straight and saturated (e.g., $C_{16}$–$C_{24}$) fatty acids, fatty acid soaps or ester derivatives thereof; and/or branched long chain, preferably straight and saturated alcohol or ether derivative.

It may be polyalkylene glycol of MW 2000 to 20,000.

Other ingredients which may be used as structurants and or fillers include starches, sugars, maltodextrins and other polysaccharides. They may also include waxes and unsaponified fats.

Inorganic fillers such as talc, kaolin, clays and calcium salts may also be used.

Structuring aids can also be selected from water soluble polymers chemically modified with hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® (PEG modified glyceryl cocoate, palmate or tallowate) from Rewo Chemicals.

Other structuring aids which may be used include Amerchol Polymer HM 1500 (Nonoxynyl Hydroethyl Cellulose).

Optional Ingredients

In addition, the bar compositions of the invention may include optional ingredients as follows:

- sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers as conditioners which may be used include Quatrisoft LM-200 Polyquaternium-24, Merquat Plus 3330-Polyquaternium 39; and Jaguar® type conditioners.

Polyethylene glycols as conditioners which may be used include:

| | | |
|---|---|---|
| Polyox | WSR-205 | PEG 14M, |
| Polyox | WSR-N-60K | PEG 45M, or |
| Polyox | WSR-N-750 | PEG 7M. |

Other ingredients which may be included are exfoliants such as polyoxyethylene beads, walnut shells and apricot seeds.

In a specific embodiment the invention relates to fatty acid soap/fatty acid based bars comprising:

(1) 20 to 75% by wt. fatty acid/fatty acid soap;

(2) 0 to 20% synthetic active;

(3) balance water and fillers (as defined);

wherein percent active of soluble active of (1) and (2) and (3) of if any) is less than about 35% by wt. total bar; and where PEF ≧2.2 relative, preferred >2.3, more preferably >2.5 to a standard control bar.

In a third embodiment of the invention, the invention relates to a process of enhancing perfume performance (e.g. deposited/longevity) from a bar comprising:

(1) surfactant active;

(2) perfume;

(3) water; and (4) filler wherein said process comprises decreasing the level of soluble surfactant active relative to insoluble surfactant active and/or filler. Specifically, the bar should have level of soluble active less than 35%, preferably less than 30%, of final bar composition and PEF ≧2.2 relative to a standard control.

In a fourth embodiment of the invention, the invention relates to an process of enhancing perfume deposition/longevity from a bar comprising:

(1) surfactant active;

(2) perfume;

(3) water; and (4) filler wherein said process comprises increasing level of perfume.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight. Further, all ranges are to be understood to encompass both the ends of the ranges plus all numbers subsumed within the ranges.

EXAMPLES

Example 1

To better understand how bar compositions can affect longevity of perfume, studies were conducted on the overall effects of soluble and insoluble surfactant on fragrance properties using a standard 85/15 soap bar (85% tallow and 15% coconut oil).

In considering fatty acid soap ratios in an 85/15 soap bar, it is easy to predict how much soap will be solubilized upon dilution or in use. Since 50–60% of the bar is sodium oleate and sodium laurate (soluble soaps), it can be assumed at least this amount will solubilize with enough water.

Studies were performed to determine how much perfume partitioned into the is soluble and the insoluble portions of the diluted soap systems. With these learnings, two model "mortar" systems and three model soap systems were then investigated to determine the effects of soluble and insoluble surfactant in a bar on actual perfume performance. To understand where the perfume partitioned during soap bar use, a 5% dilution of fragrance 85/15 soap was made, filtered and solid rinsed. The three samples (solid, filtrate, rinse) were extracted (using a Soxtherm extractor) to see the amount of perfume in each phase. Extraction of filtered 85/15 soap showed that about 74% of the perfume was in the filtrate which contains about 45% of the soap (soluble portion). Thus, upon dilution, soluble soap to perfume ratio is actually 50 to 55:1 as could be predicted by the fatty acid distribution in a typical 85/15 (tallow/coconut oil) soap. This is seen from FIG. 1. This thus clearly showed partitioning of perfume into soluble fraction.

Example 2

Using the perfume partitioning information of Example 1 (e.g., most perfume went with soluble surfactant and therefore was not available for the enhanced perfume effect), applicants established a set of model studies with a range of soluble soap systems having different soap:perfume ratios. Specifically, a soluble soap model with 1:1 ratio sodium laurate and sodium oleate was used with soap:perfume ratio 20:1 to 60:1 and compared to 85/15 soap bar containing 1% perfume (1:1 benzyl acetate:limonene mixture). Five soap dilutions were made for each sample, 40%, 25%, 10%, 5% and 1%. FIG. 2 shows the equilibrium headspace measurements for each sample at every dilution point (graphed as mg perfume in sample instead of percent dilution).

As can be seen, as the surfactant:perfume ratio increase (a function of more soluble soap components) for each of these perfume components, perfume impact or GC (gas chromatography) area count decreases and that, at soap:perfume ratio of 60:1, perfume impact approaches that of 85/15 bar.

Without wishing to be bound by theory, it is believed that, since limonene is so volatile, it reaches perfume saturation at low perfume levels and thus, even in 5% soap samples, perfume headspace plateaus. Benzyl acetate is less volatile so, in most samples, headspace saturation has not yet been achieved. Even under these conditions, it is clear for both molecules that the amount of soluble surfactant greatly impacts perfume performance and that a soap:perfume ratio of 60:1 more clearly represents results from a bar than any other total sample.

Example 3

The experiments of Example 2 were repeated with a 2:1 sodium oleate:sodium laurate system. The 2:1 base system showed similar trends in perfume performance, again indicating that increasing the surfactant:perfume ratio results in decreasing perfume impact of a benzyl acetate:limonene mixture (1:1)(FIG. 3).

Example 4

A mathematical model for similar dilution profiles as shown FIG. 4 was used to calculate the theoretical perfume performance based on the perfume type and the perfume-:surfactant ratio. Dilution curves were calculated for sodium dodecylsulfate (SDS)/benzyl acetate and SDS/limonene. These curves correlate very well with the experimental values obtained. The calculated data is depicted as solid lines in the figures while the symbols represent actual data points (FIG. 4). This validates the assumption that the actual surfactant:perfume ratio achieved during use with an 85/15 bar is ~50–60:1 and this is most likely driving the perfume performance.

Example 5

Effect of Soluble/Insoluble Soap on Perfume Performance in Bars

The GC analysis of model soap systems and theoretical predictions indicate that the amount of soluble soap in a bar directly correlates to the perfume performance. That is, the higher the soluble soap content in a bar, the lower the fragrance impact and hence deposition. To test this theory in real soap bars, several simplified soap systems were identified that contained varying levels of soluble/insoluble soap. The simplest approach toward preparing these bars was to add insoluble long chain soaps (sodium stearate) to the 2:1 sodium oleate:sodium laurate model mortar. Three model bar systems were chosen and compared directly to a standard 85:15 soap. The first model bar was a "low solids" sample composed of 20% sodium stearate and 80% 2:1 sodium oleate/sodium laurate and the second was a "high solids" sample composed of 80% sodium stearate and 20% 2:1 sodium oleate/sodium laurate. In addition to these systems, an 85/15 model system composed of 47.5% sodium ASAD (mixture of sodium stearate and sodium palmatate)/14.9% sodium cocoate/37.6% sodium: oleate was prepared. The addition of the 85/15 model system was to determine if small changes in the composition of soap with similar I.V. values (iodine values—relate to level of unsaturation) would effect perfume performance. The two perfumes tested in these bases were 1:1 benzyl acetate:limonene mix and a standard perfume mixture, both dosed at 1 wt. %.

After preparation of these soap bar systems, equilibrium GC headspace measurements were conducted on the solid samples at different bar dilutions (40%, 25%, 10%, 5%, and 1%). As predicted, decreasing the level of soluble soap ("high solids" bar) directly enhances the perfume impact in the soap base. The GC results show that the 85/15, the 85/15 model system and the "low solids" bars all have similar perfume head space profiles, while the "high solids" bar with only 20% soluble soap has significantly higher fragrance headspace (FIG. 5).

Example 6

Decreasing Ratio by Adding Perfume

Another way to decrease the soluble soap:perfume ratio is to add more perfume to the bar. If the goal is to get comparable perfume performance in a soap bar to that in a shower liquid, matching the soluble surfactant:perfume ratio is important. Typical shower liquids are formulated with 15–20% surfactant and 1% perfume, so the soluble soap-:perfume ratio is ~20:1. To mimic this in a standard 85:15 soap bar in which the soluble soap: perfume ratio is ~65:1, 4% perfume would have to be formulated in the bar (i.e. soluble soap:perfume ratio of ~65:4). So a standard 85:15 soap bar with 4% perfume was prepared to test the theory. As expected, decreasing the ratio of surfactant: perfume from 85:1 to 20:1 significantly increases the perfume head-space over the product compared to an 85:15 soap bar with 1% perfume (FIG. 10).

Example 7

Solid Phase Microextraction Results

Perfume performance over washed skin is the ultimate test to determine if the experimental differences measured as impact from diluted products can predict actually fragrance deposition in an in-use situation. Solid phase microextraction (SPME) is used to collect perfume over skin after it is washed with a product and the SPME needle is then injected in the GC for analysis.

This SPME experiment was performed with the "high solids" bar (~20:1 soluble soap:perfume ratio) versus an 85/15 control (~65:1 soluble soap:perfume ratio) both with 1% perfume (FIG. 6). The surfactant:perfume ratio is 20:1 in the "high solids" bar, achieved by lowering the amount of soluble surfactant in the actual bar. Again, as expected, the analysis results indicate that lowering the amount of soluble surfactant in a bar significantly increases perfume deposition.

Another way to decrease the soluble soap:perfume ratio is to add more perfume to the bar. If the goal is to get comparable perfume performance in a soap bar to that in a shower liquid, matching the soluble surfactant:perfume ratio is important. To mimic a low active bar with only 20% soluble active and 1% perfume, a standard 85:15 soap bar in which the soluble soap: perfume ratio is ~65:1 would have to be formulated with 4% perfume in the bar (i.e. soluble soap:perfume ratio of ~65:4). So a standard 85:15 soap bar with 4% perfume was prepared to test the theory and a similar SPME deposition experiment was conducted on arms washed with 0.5 g of an 85/15 soap bar containing 1% perfume and 0.12 g of an 85/15 bar with 4.25% perfume (FIG. 7). Therefore in both experiments, an equal amount of perfume was dosed to the skin with the only difference between the samples being the surfactant:perfume ratio. The results of this SPME analysis suggests that when formulated perfume amount was increased so that soluble surfactant-:perfume ratio is ~20:1 in a soap bar, the amount of perfume deposited on the skin increases significantly although the results are not as great as lowering over soluble active content in the bar.

While increasing the perfume amount in a typical 85/15 soap bars provides greater deposition, it does so at a prohibitive cost and a standard soap bar with 4% perfume smells very strong (too strong for consumer liking). So more effective use of the 1% perfume typically added to a soap bar would be the preferred technology option and formulating soap bars with lower soluble active content achieves this goal.

Example 8

One example of a bar cleansing composition with low amount of soluble surfactant includes predominantly soap/fatty acid compositions which can be made by reacting components having a low mol % of unsaturated fatty acid (0–12.5 mol %) (unsaturates are generally quite soluble); 50 to 87.5 mol % fatty acid of chain length $C_{16}$ or greater; and 12.5 to 50 mol % caustic (50% resulting in full neutralization) to form a bar precursor which can then be blended with up to 25% synthetic. Such final bar has high amounts of soap/fatty acid yet processes will and lather unexpectedly well.

Such bars are described in co-pending application titled "Fatty Acid Soap/Fatty Acid Bars Which Process And Have Good Lather" to Kerschner et al., filed on the same date as the subject application, and which is hereby incorporated by reference into the subject application.

One example of such compositions (which can be prepared by neutralizing fatty acid with caustic, as noted, or by simply blending pre-formed soap with fatty acid) is as follows:

| Molar Ratio of Soap/Fatty Acid | | |
|---|---|---|
| $C_{16}/C_{18}$ | $C_{18:1}$ | NaOH |
| 75 | 0 | 25 |

| Nominal Composition | Weight % |
|---|---|
| Soap | 46 |
| Fatty Acid | 25 |
| Anionic (Fatty Alcohol Ether Sulfate) | 7.5 |
| Sodium Cocoyl Isethionate | 7.5 |
| Water | 9 |
| Sodium LAS | 5 |

Example 9

Many different personal cleansing bars were prepared and fragrance deposition was measured by collecting the fragrance above washed arms immediately after the wash using SPME and then analyzing the absorbed fiber with GC. If the deposition of fragrance from a standard 85/15 soap bar is set at 1.0, a perfume enhancement factor (PEF) can be calculated for each product by determining the ratio of perfume deposited from different personal cleansing bars compared to the standard control. Typically a consumer perceivable difference in fragrance deposition is noted if the PEF is ≧2.2–2.5. The following table lists the perfume enhancement factors for different personal cleansing formulations as averaged from several washes on different people with respect to the total soluble active content in the product. As the amount of soluble surfactant is reduced to <35%, a perceivable consumer benefit is noted (PEF ≧2.2).

| Product # | % Soluble Active | PEF (ave.) |
|---|---|---|
| 1 | 50 | 1 |
| 2 | 45 | 1.06 |
| 3 | 40 | 2.1 |
| 4 | 40 | 1.8 |
| 5 | 30 | 2.75 |
| 6 | 30 | 3.2 |
| 7 | 23 | 3.9 |
| 8 | 22 | 5.1 |
| 9 | 20 | 3.8 |
| 10 | 20 | 4.2 |
| 11 | 20 | 4.7 |
| 12 | 20 | 6.0 |
| 13 | 18 | 2.5 |
| 14 | 18 | 3.3 |
| 15 | 15 | 3.5 |

The formulation ingredients for products 1–14 are summarized as follows:

Product 1 (85/15 soap formulation) contains 84.75% 85 (Tallow)/15 (Coconut) Soap, 13.5% Water and 1% Perfume;

Product 2 contains 80% 85 (Tallow)/15 (Coconut) Soap, 8.57% Sorbitol, 4% Glycerine, 1% perfume, 1.5% triethanolamine, 1.5% propylene glycol, 1.35% water, 0.56% sodium chloride;

Product 3 contains 65.50% 85 (Tallow)/15 (Coconut) Soap, 20% Sodium Stearate, 13.5% Water and 1% Perfume;

Product 4 contains 65.5% 85 (Tallow)/15 (Coconut) Soap, 20% saponified hardened tallow, 13.5% Water and 1% Perfume;

Product 5 contains 45.5% 85 (Tallow)/15 (Coconut) Soap, 40% Sodium Stearate, 13.5% Water and 1% perfume;

Product 6 contains 45.5% 85 (Tallow)/15 (Coconut) Soap, 40% saponified hardened tallow, 13.5% water and 1% perfume;

Product 7 contains 51.9% Sodium sterate/palmate mixture, 10% Dove noodles, 7.25% Water, 7% disodium lauryl sulfosuccinate, 7% sodium laureth sulfate; 5% glycerine, 4% cocamidopropyl betaine, 3.11% fatty acid, 3% PEG 1450, 1.75% perfume;

Product 8 contains 33.65% stearic/palmatic acid mix, 18.28% sodium soap, 10.57% sodium citrate, 10% fatty acid ester sulfonate (Alpha-Step PC-48), 10% sodium cocoylisethionate, 9% water, 5% glycerine, 2% sodium dodecylbenzene sulfonate, 1% perfume and 0.5% titanium dioxide, Product 9 contains 45.4% Stearic/Palmitic acid mixture, 24.53% Sodium stearate/palmatate mixture, 20% Sodium cocoyl glycinate, 9% water and 1% perfume;

Product 10 contains 42.8% stearic/palmitic acid mixture, 23.16% sodium stearate/palmatate mixture, 20% primary alcohol sulfate sodium salt (Sasolfin 23S), 9% water, 5% glycerine, 1% fragrance and 0.5% titanium dioxide;

Product 11 contains 60% saponified hardened tallow, 25.5% 85 (Tallow)/15 (Coconut) Soap, 13.5% water and 1% perfume;

Product 12 contains 60% sodium stearate, 25.5% 85 (Tallow)/15 (Coconut) Soap, 13.5% water and 1% perfume;

Product 13 contains 55% Sucrose, 5% Polyvinylpyrolidone 40K, 15% Sodium laurate, 2% Sodium dodecylsulfate, 1.75% Perfume, 0.5% $TiO_2$, 0.2% EDTA, 0.5% EHDP and 20% Water;

Product 14 contains 40% Sucrose, 20% Maltodextran 250, 15% Sodium laurate, 2% Sodium dodecylsulfate, 1.75% Perfume, 0.5% $TiO_2$, 0.2% EDTA, 0.5% EHDP and 20% Water;

Product 15 contains 42.6% stearic/palmitic acid mixture, 23% sodium stearate/palmatate mixture, 15% primary alcohol sulfate sodium salt (Sasolfin 23S), 8% talc, 5% glycerine, 6% water and 1% perfume.

EXAMPLE 10

Sensory Panel Results

To determine whether the increase in measured fragrance release from skin is actually perceivable by humans, a trained sensory panel was used to evaluate and measure the fragrance intensity over arms washed with these products. In this study, the two products compared were Product 1 (85/15 soap control) and Product 10 (a low active bar) from Example 9. This study would provide information on whether a PEF of >2.5 is perceivable by the human nose. In this study all "washes" were washed with both products so a direct comparison of the products could be assessed without having to take into account the differences in fragrance properties in the individual people (different deposition, different fragrance smell and different background odors). This will allow a comparison of the product performance regardless of the characteristics of the individual being washed. The results are shown in Table 2 and the sensory responses were recorded as an average of the magnitude estimation score recorded by the panelists for all three washes at the different time points.

TABLE 2

Fragrance Intensity Sensory Scores for Product 1 and Product 10

| | Time After Wash | Average Sensory Score |
|---|---|---|
| Product 1 (~50% soluble surfactant) | 5 minutes | 28.5 |
| | 60 minutes | 12.2 |
| Product 10 (~20% soluble surfactant) | 5 minutes | 51.5* |
| | 60 minutes | 26.5* |

*different at the 95% confidence level

The results in Table 2 represent the average scores for the panel for all six washed arms, 5 minutes and 60 minutes after the wash. Each person was washed with both products, one product on one arm and the other product on the second arm (washed arms were randomized). As is quite evident from the results, the fragrance impact from skin washed with Product 10 was perceived greater than that washed with Product 1 and these differences valid to a 95% confidence level. The sensory panel results correspond well with the analytical measurements and similar results were noted with the other products that provided a measurable PEF of greater than 2.5.

What is claimed is:

1. Bar composition comprising:

(a) 0.5 to 35% soluble surfactant active or actives;

(b) perfume;

(c) 0.5 to 20% by wt. water;

(d) 0.1 to 99% by wt. filler, wherein solubility is defined by dissolution of surfactant active or active combination of greater than about 1% by wt. in water at 40° C.;

wherein the soluble surfactant active or actives comprise C14, C12 and/or below fatty acid soaps and/or unsaturated soaps;

wherein said bar has performance enhancement factor ≧2.2 PEF based on ratio of perfume deposited from said bar relative to that deposited from a standard control.

2. A composition according to claim 1 having no more than 30% by wt. soluble surfactant active.

3. A composition according to claim 1, wherein said surfactant active is selected from anionic, nonionic, amphoteric/zwitterionic/cationic surfactants and mixtures thereof.

4. A composition according to claim 1, wherein filler is everything other than surfactant, water or perfume.

5. A composition according to claim 4, wherein filler comprises polyethylene glycol, starch, maltodextrin, polysaccharides or mixtures thereof.

6. A composition according to claim 4, wherein the filler is a mixture of long chain saturated fatty acids and long chain saturated fatty acid soaps.

7. A composition according to claim 6, comprising 0–12.5 mol % unsaturated fatty acid and less than 5% by wt. $C_{14}$ or lower chain length in final soap/fatty acid mixture.

8. A composition according to claim 1, wherein bar has PEF ≧2.3.

9. A composition according to claim 1, wherein bar has PEF ≧2.5.

* * * * *